US 6,890,315 B1
United States Patent
Levin et al.

(10) Patent No.: US 6,890,315 B1
(45) Date of Patent: May 10, 2005

(54) METHOD AND APPARATUS FOR VEIN FLUID REMOVAL IN HEART FAILURE

(75) Inventors: Howard R. Levin, Teaneck, NJ (US); Mark Gelfand, New York, NY (US); John O'Mahony, Hackensack, NJ (US); Hans-Dietrich Polaschegg, Koestenberg (AT)

(73) Assignee: CHF Solutions, Inc., Minnetonka, MN (US)

( * ) Notice: Subject to any disclaimer, the term of this patent is extended or adjusted under 35 U.S.C. 154(b) by 579 days.

(21) Appl. No.: 09/618,759

(22) Filed: Jul. 18, 2000

Related U.S. Application Data

(60) Provisional application No. 60/206,232, filed on May 23, 2000.

(51) Int. Cl.$^7$ .............................. A61M 37/00; C02F 1/44
(52) U.S. Cl. .................... 604/6.09; 604/5.01; 604/6.11; 604/6.16; 604/6.06; 604/65; 604/66; 604/67; 210/645; 210/646; 210/649; 210/650; 210/651; 210/90
(58) Field of Search ............................... 604/6.09, 5.09, 604/6.11, 6.16, 6.06, 65–67; 210/645, 649, 650, 651, 90

(56) References Cited

U.S. PATENT DOCUMENTS

| | | | |
|---|---|---|---|
| 4,080,958 A | | 3/1978 | Bregman et al. |
| 4,086,924 A | | 5/1978 | Latham, Jr. |
| 4,619,639 A | * | 10/1986 | Nose et al. ................... 604/8 |
| 4,657,529 A | | 4/1987 | Prince et al. |
| 4,784,768 A | | 11/1988 | Mathieu |
| 4,828,543 A | * | 5/1989 | Weiss et al. ............... 604/6.09 |
| 4,936,980 A | | 6/1990 | Yoshimichi et al. |
| 5,114,580 A | | 5/1992 | Ahmad et al. |
| 5,211,849 A | * | 5/1993 | Kitaevich et al. .......... 604/5.04 |
| 5,312,550 A | | 5/1994 | Hester |

(Continued)

FOREIGN PATENT DOCUMENTS

| | | |
|---|---|---|
| EP | 0 274 178 | 7/1988 |
| EP | 0 990 444 A2 | 4/2000 |
| GB | 1 583 023 | 1/1981 |

OTHER PUBLICATIONS

Strife et al, "Experience With a Low Volume Ultrafiltration Cell in Small Children," Clinical Nephrology vol. 8:No. 3, pp. 410–413 (1977).

(Continued)

*Primary Examiner*—Angela D. Sykes
*Assistant Examiner*—Leslie Deak
(74) *Attorney, Agent, or Firm*—Nixon & Vanderhye P.C.

(57) ABSTRACT

A method and apparatus for ultrafiltration of blood operating by removing blood from a peripheral blood vessel at a rate of less than two percent of total cardiac output of a patient, extracting fluid at a rate of 0.1 liter to 1.0 liters per hour while retaining cells and proteins in the blood, and returning the concentrated blood to a secondary blood vessel is disclosed. Blood is removed and returned using small gage needles. As a pump circulates blood from the patient, a filter removes ultrafiltrate from the blood using duty cycle or pump control, and a transparent container collects the removed fluid.

44 Claims, 6 Drawing Sheets

U.S. PATENT DOCUMENTS

| | | | |
|---|---|---|---|
| 5,366,630 A | | 11/1994 | Chevallet |
| 5,476,451 A | | 12/1995 | Ensminger et al. |
| 5,536,237 A | | 7/1996 | Prince et al. |
| 5,685,989 A | | 11/1997 | Krivitski et al. |
| 5,707,086 A | | 1/1998 | Treu et al. |
| 5,725,776 A | | 3/1998 | Kenley et al. |
| 5,730,712 A | | 3/1998 | Falkvall et al. |
| 5,792,367 A | * | 8/1998 | Mattisson et al. .......... 702/100 |
| 5,830,365 A | * | 11/1998 | Schneditz .................. 210/739 |
| 5,906,589 A | | 5/1999 | Gordon et al. |
| 5,910,252 A | | 6/1999 | Truitt et al. |
| 6,090,048 A | | 7/2000 | Hertz et al. |
| 6,299,575 B1 | | 10/2001 | Bolling |
| 6,387,037 B1 | | 5/2002 | Bolling et al. |
| 6,390,969 B1 | | 5/2002 | Bolling et al. |
| 2001/0016699 A1 | | 8/2001 | Burbank et al. |
| 2001/0037079 A1 | | 11/2001 | Burbank et al. |
| 2001/0041892 A1 | | 11/2001 | Burbank et al. |
| 2002/0068015 A1 | | 6/2002 | Polaschegg et al. |
| 2002/0085951 A1 | * | 7/2002 | Gelfand et al. ............... 422/44 |
| 2002/0103453 A1 | | 8/2002 | Burbank et al. |
| 2002/0147423 A1 | | 10/2002 | Burbank et al. |

OTHER PUBLICATIONS

Strife, C.F. et al, "Experience With a Low Volume Ultrafiltration Cell in Small Children," Clinical Nephrology 8:410–413 (1977).

Lauer, A. et al, "Continuous Arteriovenous Hemofiltration in the Critically Ill Patient, Clinical Use and Operational Characteristics," Annals of Internal Medicine 99:455–460 (1983).

Verbanck, J. et al, "Pure Ultrafiltration by Repeated Puncture of a Peripheral Arm–Vein as Treatment of Refratory Edema" (Case Report), The International Journal of Artificial Organs, vol. 3, No. 6 (1980), pp 342–343.

Silverstein et al, "Treatment of Severe Fluid Overload by Ultrafiltration," The New England Journal of Medicine, vol. 291, No. 15, Oct. 10, 1974, pp. 747–751.

Blake, P. et al, "Refractory Congestive Heart Failure: Overview and Application of Extracorporeal Ultrafiltration," Critical Care Nephrology, *Advances in Renal Replacement Therapy*, vol. 3, No. 2 (Apr. 1966), pp. 166–173.

Civati G. et al, "Haemofiltration Without Substitution Fluid," Proc. EDTA–ERA, vol. 21 (1984), pp. 441–446.

Jenkins, R.D. et al, "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function By Dialysis, $4^{th}$ Ed., (1996) pp. 391–397.

Gupta, B.B. et al, "High Shear Rate Hemofiltration: Influence of Fiber Dimensions and Shear Rates," Artificial Organs, International Society for Artificial Organs, vol. 13(2) (1989), pp. 97–102.

Rimondini, A. et al, "Hemofiltration as Short–Term Treatment for Refractory Congestive Heart Failure," The American Journal of Medicine, vol. 83, Jul. 1987, pp 43–48.

Donato, L. et al, "Treatment of End–Stage Congestive Heart Failure by Extracorporeal Ultrafiltration," The American Journal of Cardiology, vol. 59 (Feb. 1, 1987), pp. 379 and 380.

L'Abbate, A. et al, "Ultrafiltration: A Rational Treatment for Heart Failure," Cardiology 1989; 76:384–390.

Chen, Y. et al, "Direct Peripheral Venopuncture: Another New Choice of Temporary Vascular Access" (Case Report), Renal Failure, 22(3), 369–377 (2000).

Piergiuseppe Agostoni et al., "Sustained Improvement in Functional Capacity After Removal of Body Fluid With Isolated Ultrafiltration in Chronic Cardiac Insufficiency: Failure of Furosemide to Provide the Same Result", Mar. 1994, The American Journal of Medicine, vol. 96, pp. 191–199.

Daniel Goldstein et al., "Venoarterial Shunting for the Treatment of Right Sided Circulatory Failure After Left Ventricular Assist Device Placement", ASAIO Journal 1997, pp. 171–176.

Michael Berkoben et al., "Hemodialysis Vascular Access", pp. 41–57.

Allan Lauer, "Continuous Arteriovenous Hemofiltration in the Critically Ill Patient", pp. 455–460.

A. L'Abbate et al., "Ultrafiltration: A Rational Treatment for Heart Failure", Cardiology 1989, pp. 384–390.

Yung–Chang Chen et al., "Direct Peripheral Venopuncture: Another New Choice of Temporary Vascular Access", pp. 369–377.

James Cimino et al., "Simple Venipuncture For Hemodialysis", The New England Journal of Medicine, Sep. 20, 1962, pp. 608–609.

Drukker et al., "Replacement of Renal Function by Dialysis", pp. 334–379.

Andrea Rimondini et al., "Hemofiltration as Short–Term Treatment for Refractory Congestive Heart Failure", Jul. 1987, The American Journal of Medicine, vol. 83, pp. 43–48.

Marc Silverstein et al., "Treatment of Severe Fluid Overload by Ultrafiltration", Volumne 291, No. 15, Oct. 10, 1974, pp. 747–751.

Jonathan D. Sackner–Bernstein, MD et al., "How Should Diuretic–Refractory, Volume–Overloaded Heart Failure Patients Be Managed?" The Journal of Invasive Cardiology, vol. 15, No. 10 (Oct. 2003), pp. 585–590.

Brian E. Jaski, MD et al., "Peripherally Inserted Veno–Venous Ultrafiltration for Rapid Treatment of Volume Overloaded Patients", Journal of Cardiac Failure, vol. 9, No. 3, (Jun. 2003), pp. 227231.

* cited by examiner

US 6,890,315 B1

METHOD AND APPARATUS FOR VEIN FLUID REMOVAL IN HEART FAILURE

RELATED APPLICATION

This application is related and claims priority to the commonly-owned provisional application Ser. No. 60/206,232, entitled "Peripheral Vein Fluid Removal in Heart Failure", that was filed in the U.S. Patent and Trademark Office on May 23, 2000, and the entirety of which is incorporated by reference herein.

FIELD OF THE INVENTION

This invention relates to methods and apparatus for treatment of congestive heart failure (CHF). In particular, the invention relates to the removal of excessive fluids, such as water, in patients suffering from CHF.

BACKGROUND OF THE INVENTION

Congestive Heart Failure (CHF) is the only form of heart disease still increasing in frequency. According to the American Heart Association, CHF is the "Disease of the Next Millennium". The number of patients with CHF is expected to grow even more significantly as an increasing number of the "Baby Boomers" reach 50 years of age.

CHF is a condition that occurs when the heart becomes damaged and reduces blood flow to the organs of the body. If blood flow decreases sufficiently, kidney function becomes impaired and results in fluid retention, abnormal hormone secretions and increased constriction of blood vessels. These results increase the workload of the heart and further decrease the heart's pumping ability and, that in turn, causes further reductions in blood flow to the kidney. It is believed that the progressively-decreasing perfusion of the kidney is the principal non-cardiac cause perpetuating the downward spiral of the "Vicious Cycle of CHF". Moreover, the fluid overload and associated clinical symptoms resulting from these physiologic changes are the predominant cause for excessive hospital admissions, terrible quality of life and overwhelming costs to the health care system due to CHF.

While many different diseases may initially damage the heart, once present, CHF is split into two types: Chronic CHF and Acute (or Decompensated-Chronic) CHF. Chronic Congestive Heart Failure is a longer term, slowly progressive, degenerative disease. Over years, chronic congestive heart failure leads to cardiac insufficiency. Chronic CHF is clinically categorized by the patient's ability to exercise or perform normal activities of daily living (such as defined by the New York Heart Association Functional Class). Chronic CHF patients are usually managed on an outpatient basis, typically with drugs.

Chronic CHF patients may experience an abrupt, severe deterioration in heart function, termed Acute Congestive Heart Failure, resulting in the inability of the heart to maintain sufficient blood flow and pressure to keep vital organs of the body alive. These acute CHF deteriorations can occur when extra stress (such as an infection or excessive fluid overload) significantly increases the workload on the heart in a stable chronic CHF patient. In contrast to the stepwise downward progression of chronic CHF, a patient suffering acute CHF may deteriorate from even the earliest stages of CHF to severe hemodynamic collapse. In addition, Acute CHF can occur within hours or days following an Acute Myocardial Infarction (AMI), which is a sudden, irreversible injury to the heart muscle, commonly referred to as a heart attack.

A. Treatment Strategies for CHF

1. The Treatment of Chronic CHF

There are currently two broad categories for the treatment of Chronic CHF: (1) drug therapy and (2) surgical therapy. All treatments share the common goal of the alleviation of CHF symptoms, the improvement of heart function, and the disruption of the neurohormonal secretions of a kidney to decrease stress and prevent possible failure.

A cornerstone of the drug therapy of Chronic CHF includes the use of angiotensin converting enzyme (ACE) inhibitors, positive inotropic agents, diuretics, digitalis, and, more recently, beta-blockers with the amount of each drug used dependent on the stage of heart failure.

Positive Inotropic Agents

Directly combating the inability of the heart to propel blood forward might seem to be the single most intuitive means for treating heart failure. A class of drugs known as inotropes increases the strength of contraction of the remaining viable heart muscle, allowing the heart to expel more blood with each beat. While all types of inotropes (e.g., dobutamine, dopamine, milrinone) are effective in the short-term, they lack long-term value in the treatment of heart failure because they, like the vasodilators, tend to cause additional neurohormonal activation (as evidenced by hormonal kidney secretions) and perpetuation of the downward spiral.

Diuretics

Diuretics decrease the sodium and water retention in a patient by preventing reabsorption of these substances at specific sites in the renal tubules of the kidney. Diuretics, such as Lasix and Bumex, are effective at reducing symptoms of heart failure due to fluid overload, especially in the lungs and extremities. In the long-term, diuretic therapy fails because it further activates the renin-angiotensin system (e.g., the hormones secreted by the kidney) and eventually overwhelms the ability of diuretics to control salt and water retention.

Vasodilators

The next logical step in the treatment of heart failure is to limit vasoconstriction and reduce its adverse effect on the heart. Unfortunately, vasodilatory agents, like diuretics, fail after a period of time, as they decrease kidney perfusion pressure and activate the renin-angiotensin system.

ACE Inhibitors and β-Blocking Drugs

In the past two decades, the development of angiotensin converting enzyme (ACE) inhibitors and β-blockers has signaled perhaps the most significant development of this century in the pharmacological treatment of heart failure. Both are aimed at the neurohormonal axis of this disease and both act by disruption of the feedback loops that characterize heart failure. β-blockers and ACE inhibitors are the first classes of drugs to be associated with a survival benefit for patients in heart failure. However, despite these significant advances in medical therapy, their effectiveness is limited, especially in the later stages of CHF. Patients become resistive to the increased dose and potency of drugs until further increase becomes too dangerous.

Surgical Therapies

There are three potential surgical treatments for patients in heart failure: (1) revascularization, (2) implantation of a heart assist device, and (3) heart transplantation. Revascularization is the restoration of blood flow to the heart itself, either angiographically (PTCA) or surgically (CABG). Revascularization is performed in patients in whom it is believed that a poor blood supply to the heart itself is the major cause of the observed heart dysfunction. A second surgical modality is the placement of an implantable pump that replaces the failed ventricle. This type of device is known as the Left Ventricular Assist Device (LVAD). The third and ultimate surgical modality for patients suffering from heart failure is transplantation. While this can be an effective means to cure heart failure, transplantation is replete with significant medical issues. In addition, for a majority of patients suffering from CHF, transplantation is not available because they fail to meet current criteria for heart transplant recipients, socioeconomic issues and, most commonly, lack of donor organs. Despite their benefit, surgical therapies are used in less than 1% of all heart failure patients due to their cost, invasiveness and a lack of donors' hearts.

2. Treatment of Acute CHF

Pharmacologic Therapies

In contrast to the treatment of Chronic CHF, the abruptness and severity of the decrease in blood flow and pressure put the vital organs, e.g., the kidneys, at immediate risk of severe damage. Interestingly, the physiologic effects of some therapies used to treat Acute CHF closely parallel those of the "Vicious Cycle" of CHF in that they may transiently or permanently damage some organs to preserve the heart and the brain.

The first line of therapy for Acute CHF is the use of intravenous (IV) inotropic ("squeeze" enhancing) agents in concert with intensive diuretic therapy. The purpose of this therapy is to substantially increase the output of the heart, increasing kidney blood flow, and thereby increasing urine output. It may take hours to days for this therapy to restore hemodynamic stability and fluid removal. In addition, therapy with IV inotropic agents has side effects. Most inotropic drugs can cause vasodilation and hypotension (low blood pressure) that may lead to Acute Renal Failure. Cardiac arrest from inotropic-induced arrhythmias (irregular heartbeats) also can occur.

The second-line therapy is the use of vasopressor (vasoconstricting) agents. While they increase blood pressure, in the higher doses used in Acute CHF, these agents cause severe vasocontriction, and can lead to kidney and liver failure. In concert with a large mandatory fluid intake from multiple IV medications, progressively increasing diuretic unresponsiveness and concurrent hemodynamic instability, reduced renal perfusion leads to the refractory (drug resistive) fluid overload state seen in Acute CHF. This excess fluid decreases ventricular function, oxygenation and other organ function, and impairs the ability to give such additional therapies as increased IV pharmacologic therapy (such as vasopressors) or parenteral nutrition.

3. Mechanical Fluid Removal Therapies

Once pharmacological therapy is exhausted, Continuous Renal Replacement Therapy (CRRT) has been used to treat patients suffering from excess fluid overload. CRRT has been performed previously using standard methods of hemodialysis and continuous arterio-venous hemofiltration (CAVH). More recently, continuous veno-venous hemofiltration (CVVH) has been used to reduce the complications associated with such issues as hemodynamic instability and need for arterial access.

In cases where drug therapy is no longer sufficient to support the patient, effective, intra-aortic balloon pumps (IABPs) are commonly used. IABPs provide limited support of blood flow and pressure in CHF. Other devices, including ventricular assist devices are invasive and costly, but effective at increasing blood flow. Implantation of these devices generally requires the patient to undergo heart transplantation.

4. Failure of the Current Treatments for CHF

Current treatments for CHF share the common goal of the alleviation of symptoms, and the improvement of heart and kidney function. The cornerstone of the medical therapy of chronic CHF includes the use of angiotensin converting enzyme (ACE) inhibitors, positive inotropic agents, diuretics, digitalis, and more recently, beta-blockers with the amount of each drug used dependent on the stage of heart failure. While drug therapy is effective in the early stages of CHF, there is no truly effective drug treatment for the later stages of CHF. Acute CHF is generally treated with intravenous inotropic ("squeeze" enhancing) and vasopressor (blood pressure raising) agents in concert with intensive diuretic therapy. If this therapy fails, the patient can quickly develop severe fluid overload and suffer rapidly-worsening heart and kidney function. Intra-aortic balloon pumps (IABPs) are commonly used but of minimal benefit in CHF. Hemodialysis and hemofiltration have been shown to be effective in removing extra fluid, reducing symptoms and improving heart function, but its use is limited to the Intensive Care Units (ICU) patient population.

Surgical solutions exist, but are only used for the treatment of very end-stage heart failure. These therapies (such as LVADs) are very effective at increasing blood flow. However, they are invasive, costly and require the patient to undergo heart transplantation. Even with the wide variety of existing therapies, over 2,300,000 CHF patients become hospitalized each year at a cost of over $10 billion dollars to the health care system. New CHF therapies are needed.

B. A Large Unmet Clinical Need in Patients with CHF for Enhanced Fluid Removal

If excessive fluid is not promptly removed with medication, CHF patients are often intubated and placed on a ventilator. If the initial diuretic therapy has little affect, more aggressive treatment with increasingly potent diuretics is needed. In addition, inotropic agents such as dobutamine are administered to increase the pumping function of the heart and rise the blood pressure. Higher blood pressure is expected to assist in the perfusion of the kidneys and make diuretics work. In more recent years vasodilator therapy became a part of the standard therapy for a severely volume-overloaded, decompensated CHF patient. All the above-mentioned therapies as a rule require admission to the ICU. Potentially dangerous side affects of drugs, needed for advanced monitoring and intubation, are the main reasons for a typical ICU admission.

While there are many potential factors that cause a patient to be hospitalized, the primary causes of admission in CHF patients are symptoms of severe shortness of breath from fluid overload. Standard drug therapy is unable to remove excess fluid rapidly enough to prevent hospitalization before any increased standard medical therapy has time to work. There is a clear and unmet clinical need for a CHF treatment that allows physicians to rapidly, controllably and safely remove a clinically significant amount of fluid from a CHF patient. Such a treatment would reduce the need for excessive hospital admissions.

Symptoms of fluid overload are excessive fluid retained in the abdomen, legs and lungs. Of these, fluid in the lungs is the most important. Patients have difficulty breathing. Edema in the lungs leads to poor blood oxygenation. Poor oxygenation leads to acidosis and deleterious neurological and hormonal phenomena that increases vasoconstriction and load on the heart. In addition, vasoconstriction leads to reduced blood flow to the kidneys and diminishes the effectiveness of the main pharmacological means of fluid removal—diuretic treatment. This phenomenon is known as the "vicious cycle" of CHF heart failure.

As previously mentioned, hemodialysis and hemofiltration can be used to remove excess fluid from a patient, especially in patients whose kidneys are not working. The term "Renal Replacement Therapy" generally refers to any forms of dialysis, solute and fluid balancing therapy. These treatments circumvent the kidney and replace kidney functions. These treatments are not generally applicable to CHF patients having functional kidneys, but which lack sufficient blood flow to properly perform their kidney functions, especially the removal of excess fluids, e.g., water, from the body.

1. Principles and Concept of Existing Methods of Renal Replacement Therapy

Renal replacement therapy performs two primary functions: ultrafiltration (removal of water from blood plasma), and solute clearance (removal of different molecular weight substances from blood plasma). The filter called "dialyzer" can be set up to perform either or both of these functions simultaneously, with or without fluid replacement, accounting for the various modes of renal replacement therapy. "Clearance" is the term used to describe the removal of substances, both normal and waste product, from the blood.

Ultrafiltration is the convective transfer of fluid out of the plasma compartment through pores in the membrane. The pores filter electrolytes and small and middle sized molecules (up to 20,000 to 30,000 daltons) from the blood plasma. The ultrafiltrate output from the filtration pores is similar to plasma, but without the plasma proteins or cellular components. Importantly, since the concentration of small solutes is the same in the ultrafiltrate as in the plasma, no clearance is obtained, but fluid volume is removed.

Dialysis is the diffusive transfer of small solutes out of a blood plasma compartment by diffusion across the membrane itself. It occurs as a result of a concentration gradient, with diffusion occurring from the compartment with higher concentration (typically the blood compartment) to the compartment with lower concentration (typically the dialysate compartment). Since the concentration of solutes in the plasma decreases, clearance is obtained, but fluid may not be removed. However, ultrafiltration can be combined with dialysis.

Hemofiltration is the combination of ultrafiltration, and fluid replacement typically in much larger volumes than needed for fluid control. The replacement fluid contains electrolytes, but not other small molecules. Since the net effect of replacing fluid without small solutes and ultrafiltration of fluid with small solutes results in net removal of small solutes, clearance is obtained.

While effective at removing excess fluid, substantial clinical data exists showing that ultrafiltration provides significant other benefits to patients with CHF. These benefits include the promotion a variety of compensatory neurohumoral mechanisms, such as activation of the renin-angiotensin-aldosterone system and stimulation of the sympathetic nervous system, resulting in both sodium accumulation and increased peripheral vascular resistance. Commonly, fluid removal with diuretics further enhances the neurohumoral stimulation and may even aggravate heart failure in some patients. Ultrafiltration interrupts this vicious cycle and represents an alternative approach to the treatment of refractory heart failure. Further beneficial effects of ultrafiltration include a subsequent increase in urine output, and an increased responsiveness to standard oral diuretic therapy.

For example, one study randomized congestive heart failure (NYHA Class II to III) to treatment with ultrafiltration (1.3 to 2.6 L over 3 to 5 hours) or with furosemide (potent diuretic). Both treatments produced similar hemodynamic and fluid losses. However, three months after intravenous furosemide treatment, hemodynamics and fluid volume had worsened back to baseline values, yet they were still significantly improved in the ultrafiltration group. The data suggest that fluid removal by ultrafiltration shifts the abnormal set point for fluid balance to a more physiologic level, an effect not accomplished by furosemide, despite comparable amounts of volume removal. Several other clinical studies showed similar beneficial results. Thus, ultrafiltration appears to be a beneficial in patients with CHF, even those still responsive to standard medical therapy.

2. Limitations of Existing Methods of Ultrafiltration to Treat CHF

Ultrafiltration has not been used widely in the treatment of patients with CHF, despite its apparent clinical benefits. There are several issues limiting the use of currently available ultrafiltration devices:

i. Prior ultrafiltration devices require central venous access (e.g., via surgery) with its attendant risk of infection, bleeding, collapsed lung and death.

ii. Prior ultrafiltration treatments require interaction and use by a nephrologist who is not the patient's primary physician, and who may be reluctant to expend their device and personnel resources on these patients.

iii. Prior ultrafiltration devices draw large blood volumes of blood out of the body and, thus, require central venous access. Moreover, the temporary large blood loss may lead to hypotension (low blood pressure) and the potential for large losses of blood.

iv. Prior ultrafiltration devices are generally designed to be only used in the ICU or dialysis unit environment.

v. Prior ultrafiltration devices require high blood volume flows to prevent clotting in the blood circuit and filter apparatus.

vi. Most patients are required to be anticoagulated leading to an increased risk of bleeding.

Continuous Veno Venous Hemofiltration (CVVH) allows removal of blood fluid and modification of the volume and composition of extracellular fluid to occur evenly over time. A filter that is highly permeable to water and small solutes but impermeable to plasma proteins and erythrocytes, is placed in the extracorporeal circuit. As the blood perfuses the hemofilter an ultrafiltrate is removed in a manner similar to glomerular filtration in the kidney.

Modern CVVH machines over time can provide almost complete renal replacement therapy (act as an artificial kidney) in an anuric patient. The technique is typically used in the ICU setting on a patient that has permanently or temporarily lost natural renal function as an alternative to intermittent dialysis. Secondary to the artificial kidney function, CVVH offers precision and stability that allows electrolytes or any appropriately sized element of circulation to be removed or added independently of changes in the volume of body water. In turn, if desired, the volume of water can be adjusted in a controlled fashion. Although valuable and powerful clinical tool, the versatility of CVVH limits its use in clinical practice and acceptance. The limitations of CVVH include:

i. Electrolyte removal and replacement is a high risk therapy. It is particularly risky in cardiac patients, since excess or depletion of electrolytes can cause arrhythmias. For this reason primarily, CVVH is prescribed and administered by a nephrologist.

ii. Large amounts of blood, in the range of 100–400 mL/min or as much as 10% of the total cardiac output for an adult patient, are passed through the filter. This necessitates the so-called "central" vascular access. Relatively-large and long catheters are threaded from a peripheral vein in an arm or a leg of the patient until they reach a large vascular volume in the center of the body where the sufficient blood flow is present. These cavities containing large volumes of blood can be the vena cava or the right atrium of the heart. To establish the central access a vascular surgeon or another similar specialist is required. Patients with central access catheters require additional monitoring. The central access is associated with serious complications.

iii. Tens of liters of fluid are continuously removed and replaced in a patient over the course of one day. If the desired balance is disrupted, patient can rapidly gain or lose fluid. The part of the machine responsible for fluid balance is called an ultrafiltration controller (UC). The UC of a modern CVVH machine has evolved into an extremely sophisticated apparatus capable of measuring the rate at which fluid is added or removed with the accuracy of less than 0.5%. This accuracy comes at a price of technical complexity and cost.

As a result, CVVH has in the past only been used in the ICU of a hospital where resources, training and adequate nursing monitoring are available. In addition, controls of CVVH machines are difficult to understand and require extensive training. Although the latest and most sophisticated apparatus "Prisma" from Gambro takes advantage of interactive computer screens to simplify the task of setting up the device and controlling its use, it still requires many parameters to be configured before the device can be used.

Mechanical fluid removal such as SCUF (Slow Continuous Ultrafiltration) or CVVH is not used in these patients until it becomes obvious that the natural kidney function is insufficient. This typically is a result of an Acute Renal Failure (ARF) secondary to hypotension and hypoperfusion of the kidneys. The CVVH is prescribed by a nephrologist.

Abundant scientific and clinical evidence exists that aggressive early fluid removal with a machine would benefit CHF patients. It can reduce symptoms of fluid overload, prevent intubation, reduce load on the heart and reduce neuro-hormonal stimuli that drive vasoconstriction. To be truly affective the treatment shall precede the onset of ARF and shall be placed in the hands of a cardiologist who is the primary physician responsible for a CHF patient.

Current clinical use of CVVH in heart failure can be described as "too little too late". As a result, CVVH is used for many days not as much for fluid removal but as an acute renal replacement therapy (similar to dialysis) in patients with lost renal function.

With the increasing prevalence of decompensated CHF and the increased cost of hospital admission and even more so of ICU treatment, a strong need has emerged for a new technology that will allow fluid removal in the non critical care setting. This need is for a device and technique that is simple and safe so that it could be used in the outpatient setting, doctors offices, Emergency Rooms (ER) and general hospital floors.

SUMMARY OF THE INVENTION

To better address this important therapeutic modality and eliminate these significant limitations, the inventors have developed a novel method and device that safely performs ultrafiltration using only the blood drawn from a peripheral vein.

One advantage of the invention is that it does not require surgery or ICU, and can be administered to patients in emergency rooms, clinics and other such facilities. The majority of the total of the 2.5 million CHF patients admitted per year in the United States do not require an ICU. The admission of many of these cases to the hospital could be adverted altogether if there existed a safe, simple means to remove excess fluid from these patient to relieve the CHF symptoms of fluid overload.

The invention includes a device that is suited to extract excess fluid from a CHF patient at a clinically relevant rate that will overcome the deficiencies of existing machines for renal replacement therapy and particularly could be used outside of an ICU. The invention provides a simple excess fluid extraction (SAFE) system for use with CHF patients.

The invention avoids the need for a central access to venous blood. Central access catheters such as 10 or 14FR catheters from Medcomp PA can are primarily used in the ICU or special dialysis setting. Thus, a device requiring central access to venous blood was generally not used to treat CHF patients, other than the most sick CHF patients.

The invention provides an acceptable level of invasiveness for a fluid removal treatment in the desired environment and patient population via a peripheral vein preferably in an arm of a patient. Such access is commonly established by a nurse to draw blood or to infuse drugs. The invention does not require an ICU or a special dialysis setting to be administered to a patient. If an apparatus for slow continuous ultrafiltration was available that would draw and re-infuse blood into the body using the access site similar to a common IV therapy, such device would have a widespread clinical use.

Extracorporeal blood treatment are known in the prior art where blood is continuously withdrawn from, processed and returned into the same or different vein in the patient's arm. For example, such methodology is commonly used in blood apheresis treatment. Examples of apparatus for plasma apheresis are Spectra or Trima from Gambro. The major limitation of peripheral access is the relatively modest amount of blood that can be withdrawn per unit of time. It is accepted that in almost all patients the blood flow of 40–60 mL/min can be established. In some cases blood flow of up to 100 mL/min can be achieved. Blood flow available from a peripheral vein is therefore a great deal lower than the blood flow of 100–400 mL/min that is required to operate renal replacement therapy machines such as Prisma or BP11 in an adult patient.

This apparently insufficient blood flow from a peripheral vein was perceived by the engineering and medical community as a prohibiting factor. In spite of an apparent clinical need, the peripheral vein ultrafiltration was never developed or even investigated. Rather than take the blood flow requirement on the "face value", applicants analyzed the medical and engineering considerations behind the requirement for blood flow. They developed a clinically-useful method and apparatus for fluid removal that can operate at blood flows of less than 100 mL/min and preferably of 40 to 60 mL/min.

Existing renal replacement therapy machines and specifically ones used in acute setting to perform SCUF and CVVH therapy were all designed to primarily perform hemofiltration and hemodialysis, not fluid removal. Blood is composed of cellular components suspended in the fluid component called plasma. Water is the primary constituent of plasma in which physiological solutes such as sodium and potassium are dissolved. In plasma the larger molecules, proteins and blood cells, are suspended. Ultrafiltration and hemofiltration operate by convection. In ultrafiltration, a solute molecule is swept through a membrane by a moving stream of ultrafiltrate. Proteins and blood cells are retained by the membrane. In patients with renal failure, renal replacement therapy, such as hemofiltration or dialysis, removes undesired solute. In renal replacement therapy, vital elements such as electrolytes are removed from the blood and need to be replaced.

During hemofiltration solute removal is entirely dependent one convective transport. Hemofiltration is relatively inefficient for solute removal, as compared to dialysis. Hemodialysis allows the removal of water and solutes by diffusion across a membrane in the direction of the concentration gradient. Diffusion transfers solute molecules across the membrane in the direction of the lower solute concentration at the rate inversely proportional to the molecular weight.

Hemodialysis requires a large membrane surface to enable effective solute clearance by diffusion. Hemofiltration requires large amount of ultrafiltrate to be transferred across the membrane to remove a relatively small amount of solute. This is a consequence of convection being an inefficient method of solute transport. Large amounts of fluid such as 1 to 4 liters per hour (L/hour) are continuously being removed during CVVH. The resulting loss of water and electrolytes are immediately dangerous to the patient. To maintain fluid and electrolyte balance, equally large or slightly lower amount of replacement fluid is infused into the patient. Replacement fluid is thus added into the extracorporeal blood circuit before or after the filter.

There is a straightforward dependency between the maximum amount of ultrafiltrate removed from the blood and the flow (volume per unit time) of blood that must pass through the filter. Blood condenses in the filter as the water is removed. The water is removed as it is sieved from the blood in the filter. In practice only approximately 20% to 30% of the ultrafiltrate volume can be removed from blood safely as water. If more is removed, the blood becomes too dense with red blood cells and protein and will flow sluggishly.

Also, filter membranes are designed to pass water and small solutes as ultrafiltrate, but to retain red blood cells and proteins. This inherently limits the amount of fluid that the filter can remove per unit of surface area of the membrane. The permeability of a filter to ultrafiltrate per unit of driving Trans Membrane Pressure (TMP) is a constant called the ultrafiltration coefficient (KUF) of a filter. The KUF of blood filters has increased dramatically in recent years. In modern CVVH machines filters with KUF as high as 50 mL/hour/mmHg are used. For example, the popular Fresenius F-series of filters have KUF of 20, 30 and 40. The higher KUF of filters was achieved by using more permeable membranes. Permeability of fibers is measured in mL/hour/m$^2$/mmHg. The permeability of fiber used in Fresenius filters is 33 mL/hour/m$^2$/mmHg. Higher permeability membranes allow efficient ultrafiltration with smaller membrane surface areas. This method of increasing efficiency of ultrafiltration has inherent limitations. KUF of a membrane substantially higher than 50 mL/hour/m$^2$ mmHg cannot be achieved since the filter will eventually become permeable to proteins.

In general, an increase in the flow of ultrafiltrate requires a larger filter membrane surface. The rate of ultrafiltration can be somewhat improved by increasing the TMP, but the effectiveness of this method is also limited. When TMP increases over a value of 200–300 mmHg, the ultrafiltration rate stops increasing and will actually start dropping if TMP is increased much further. This is explained by the fouling of the membrane. Proteins are pushed into the pores of the membrane by higher TMP and the actual KUF of the membrane becomes lower than the theoretical KUF. Eventually the membrane is clogged and the ultrafiltration stops. Also high TMP leads to hemolysis and distruction of red blood cells.

These limitations are well known and accepted in the industry. As a result, filters used for CVVH in adults have the membrane surface area of 0.7–2 m$^2$. The required minimal surface area drives several design constraints of the filter. A substantial number of hollow membrane fibers (typically >3,000) are used in parallel to create the desired surface area in a bundle of practical length. This determines the area of the contact of blood with an artificial material and the time of the exposure of blood to that material for a given blood flow. Prolonged exposure to plastics is known to trigger the process of coagulation of blood. Unless undesirable high doses of anticoagulants such as heparin are used, blood flowing slowly through a filter with a substantial membrane surface area will inevitably clot. In fact, filter clotting is the number one problem of both intermittent dialysis and continuous hemofiltration. To prevent blood from clotting in the filter substantial blood flows in access of 100 mL/min are maintained through the extracorporeal circuit. As a result, although CVVH machines such as Gambro Prisma can, according to the specification, pump blood at flows as low as 10 mL/min, these flows are not practical and are never used in adults.

The above-mentioned facts frame an unsolvable problem for a designer of a CVVH machine that would function reliably for many hours and draw blood from a peripheral vein access. The blood flow available is not sufficient to provide the clinically useful rate of solute removal using any existing filter material or design. In addition, the high extracorporeal flow of blood is likely to require close monitoring of the patient even in the presence of a sophisticated ultrafiltration controller. The existing ultrafiltration controllers are based on either integration of flow or measuring weight of removed and added fluid. Both measurement methodologies are dependent on calibration and are sensitive to drift, noise and artifacts.

To overcome some of the problems with CVVH, applicants determined that the invention need not provide total renal replacement therapy. Patients with fluid overload resulting from decompensated heart failure do not suffer from acute or chronic renal failure. Their needs are different from the ICU patients that the CVVH is used on. The intrinsic kidney function of these patients would be sufficient to remove fluid and solute if the vasoconstriction of the renal artery was not limiting the blood flow to the kidney. In those patients that respond well to diuretics, kidneys usually start functioning quite adequately after the initial 2–5 liters of excessive fluid is removed.

The total renal function can in general be divided into water and solute removal. The present invention provides a water removal function, but does not provide solute removal. The apparatus of the present invention may not be capable of removing clinically significant amount of solute. The lack of solute removal in the present invention is beneficial in that it does not significantly remove electrolytes from the blood. In heart failure patients, loss of electrolytes can lead to dangerous arrhythmias. Moreover, even with very low daily urine output the kidney is capable of the solute clearance that is sufficient to sustain metabolic equilibrium. Kidney can concentrate solute in as little as 0.6 liters per day of urine. However, this amount of urine output is not sufficient to maintain the fluid balance. Accordingly, the kidneys of a CHF patient may be sufficient for solute removal needs, and require the assistance of the present invention for water (fluid) removal.

SUMMARY OF THE DRAWINGS

A preferred embodiment and best mode of the invention is illustrated in the attached drawings that are described as follows.

DETAILED DESCRIPTION OF THE INVENTION

For the proposed clinical use, the capability of the invention is to remove water drove the design. This is fortunate since the convection technique proposed here for removal of water is inefficient (in terms of the solute material removed per unit of the surface area of the membrane) in removing solute from the blood plasma. The functional kidneys of the patient are relied on to remove solutes from the plasma. The kidneys are, thus, relived of having to perform substantially all fluid removal from the blood.

Figure 1:
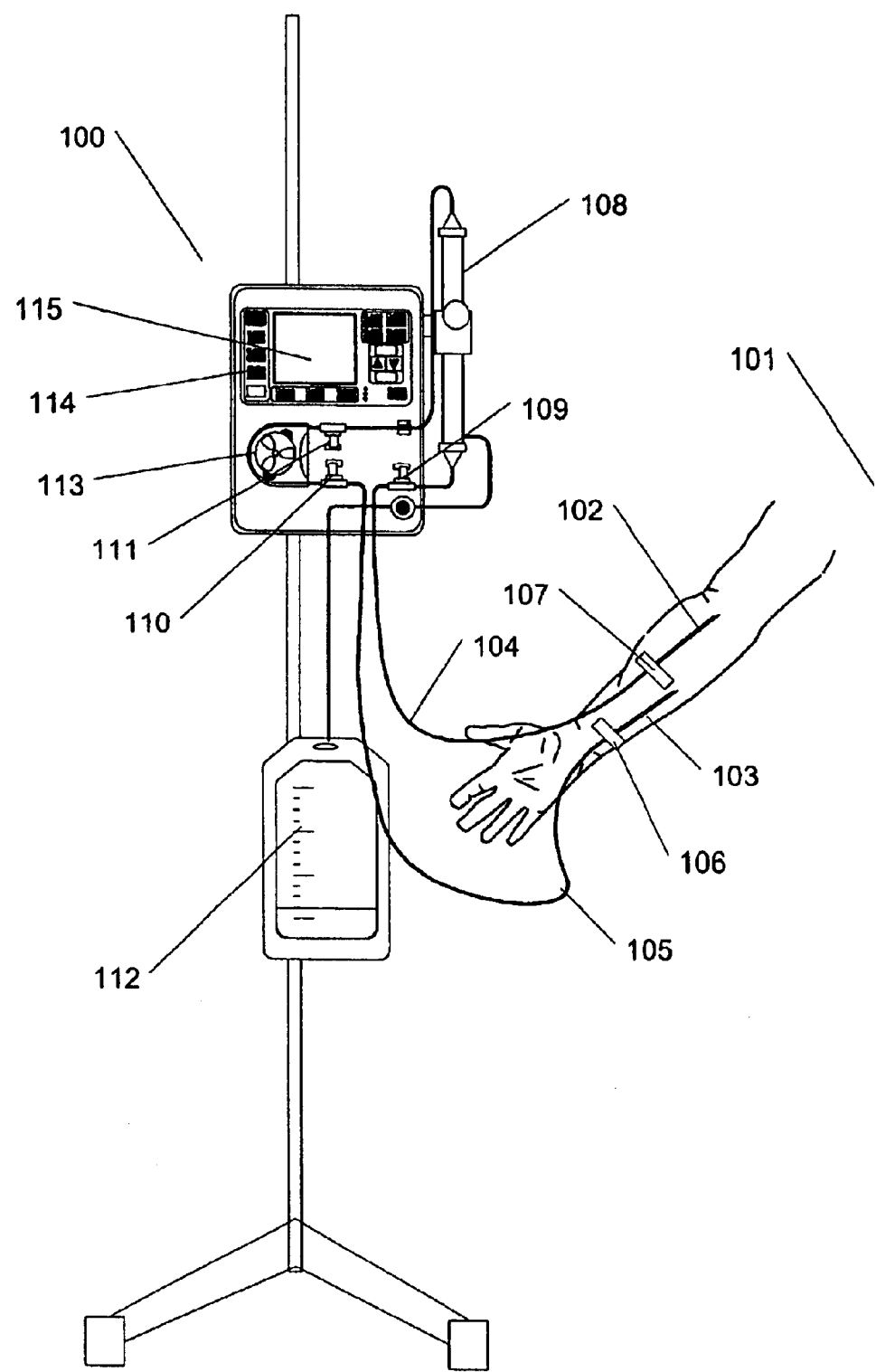
FIG. 1 illustrates the treatment of a fluid overloaded patient with the present invention.

FIG. 1 illustrates the treatment of a fluid overloaded patient with the present invention 100. Patient 101 can undergo treatment while in bed or sitting in a chair. Patient can be conscious or asleep. To initiate treatment two relatively standard 18G needles 102 and 103 are introduced into suitable peripheral veins (on the same or different arms) for the withdrawal and return of the blood. This procedure is no different from blood draw or IV therapy. Needles and attached to tubing 104 and 105 and secured to skin with attachments 106 and 107. The blood circuit that consists of the blood filter 108, tubes, pressure sensors 109, 110 and 111 and the ultrafiltrate collection bag 112. The circuit is supplied in one sterile package and is never reused. It is easy to mount on the pump 113 and can be primed and prepared ready for operation within minutes by one person.

During operation, the present invention requires minimal intervention from user. User sets the maximum rate at which fluid is to be removed from the patient using the control panel 114. Ultrafiltrate is collected into a graduated one-liter collection bag 112. When the bag is full, ultrafiltration stops until the bag is emptied. Information to assist the user in priming, setup and operation is displayed on the LCD display 115.

Figure 2:
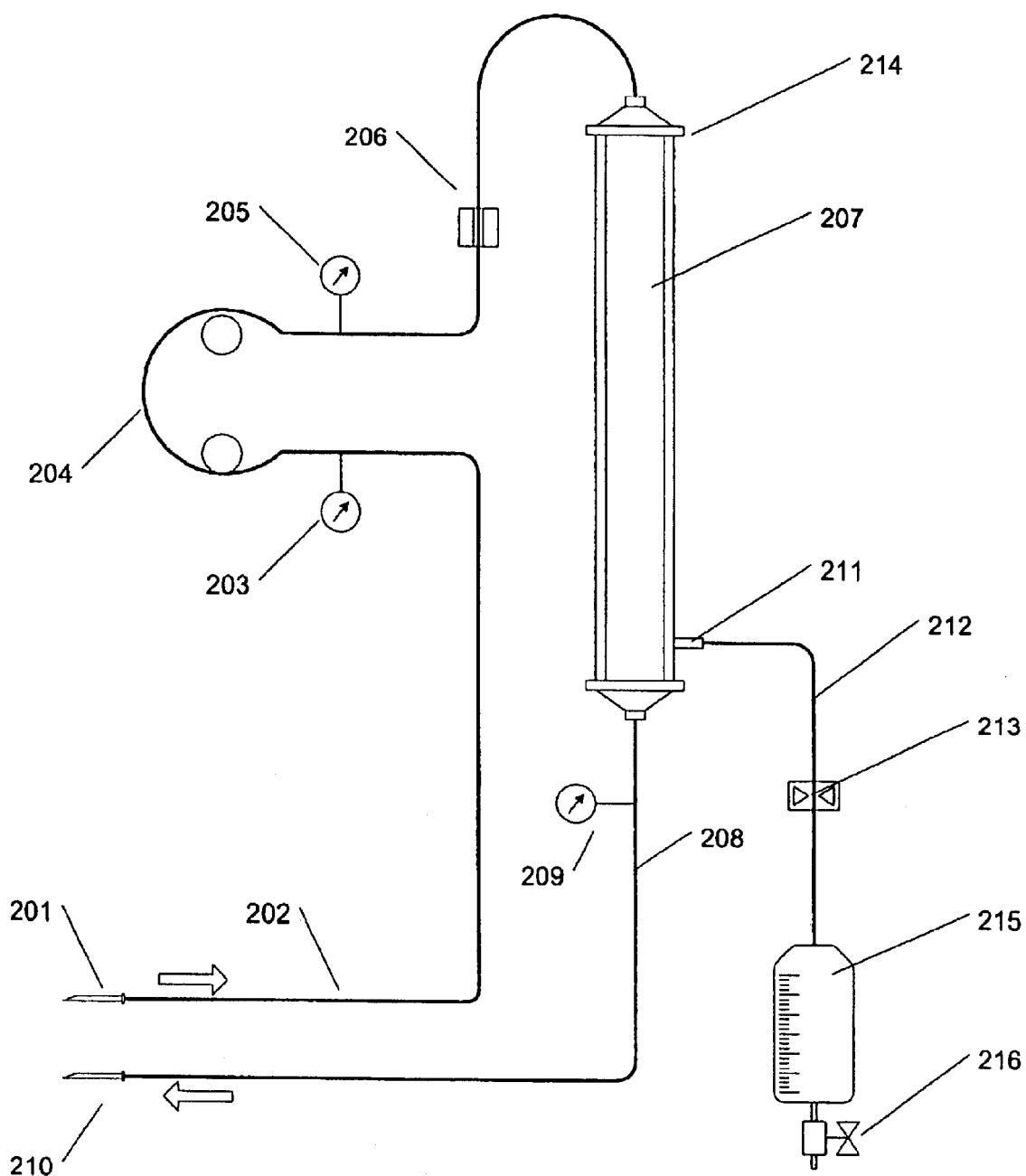
FIG. 2 illustrates the operation and fluid path of the preferred embodiment of the present invention.

FIG. 2 illustrates the operation and fluid path of the preferred embodiment of the present invention. The present invention consists of a microprocessor controlled console and a disposable kit. Disposable kit is bonded (with the exception of needles) and is supplied sterile.

Blood is withdrawn from the patient through the 18 Gage or similar withdrawal needle 201. The needle 201 is inserted into a suitable peripheral vein in the patient's arm. Blood flow is controlled by the roller pump 204. Before entering the pump blood passes through approximately two meters of plastic tubing 202. Tubing is made out of medical PVC of the kind used for IV lines and has internal diameter (ID) of 3 mm. Pump is rotated by a DC motor under microprocessor control. The pump segment (compressed by the rollers) of the tubing has the same ID as the rest of the blood circuit. The system is designed so that approximately 1 mL of blood is pumped per each full rotation of the pump, e.g. pump speed of 60 RPM corresponds to 60 mL/min.

The disposable withdrawal pressure sensor 203 is a part of the blood circuit. Pressure sensor 203 is a flow-through type commonly used for blood pressure measurement. There are no bubble trap or separation diaphragms in the sensor design, which reduce the accuracy. Pressure sensor is designed to measure negative (suction) pressure down to −400 mmHg. All pressure measurements in the fluid extraction system are referenced to atmospheric. The withdrawal pressure signal is used by the microprocessor control system to maintain the blood flow from the vein. Typically, a peripheral vein can continuously supply 60100 mL/min of blood. This assumption is supported by the clinical experience with plasma apheresis machines.

In some cases, blood flow can be temporarily impeded by the collapse of the vein caused by the patient motion. In other cases the vein of the patient may not be sufficient to supply the maximum desired flow of 60 mL/min. The software in the present invention microprocessor is designed to control the withdrawal of blood to prevent or recover from the collapse of the vein and reestablish the blood flow based on the signal from the withdrawal pressure sensor.

The same pressure signal from the sensor 203 is used to detect the disconnect of the withdrawal bloodline 202 from the needle 201. This condition is detected by the abrupt decrease of the withdrawal pressure generated by the pump. The resistance of the 18 Gage needle, which is 4 cm long with an approximately 0.8 mm ID at a flow rate corresponding to a 60 mmHg, pressure drop is on the order of the 100 mmHg. The resistance of 2 meters of blood tubing with a 3.5 mm ID at the same flow rate is on the order of 20 mmHg. This enables automatic reliable detection of the line disconnection. The occlusion of the withdrawal bloodline is detected in the similar fashion. The occlusion can be caused by the collapse of the vein or by the kinked blood tube. Occlusion results in a rapid decrease (more negative) of the pump suction pressure that is detected by the microprocessor. In response to this condition, the microprocessor stops the pump and alarms the user.

The present invention uses a double roller pump 204 to pump blood. As the pump 204 rotates, rollers compress the segment of PVC tubing and generate flow. Pump 204 is adjusted to be fully occlusive until the pressure limit is reached. The rollers are spring loaded to limit the maximum positive and negative pressure generated by pump head. This feature is not normally used to limit pressure in the circuit and is only included as a secondary safety precaution.

A direct drive stepper motor rotates the rollers, and the speed of the motor is determined by the controller microprocessor. The RPM of the pump 204 is used as a feedback signal by the controller to determine the blood flow. Normal operational blood flow in the present invention is between 40 and 60 mL/min. This minimum rate of blood flow is needed to generate Trans Membrane Pressure (TMP) needed for ultrafiltration and to prevent stagnation and clotting of blood in filter 207.

Pump pressure sensor 205 is incorporated into the post-pump segment of the blood tubing connecting pump 204 to the blood inlet port 214 of the filter 207. Like other pressure sensors in the present invention it is a flow through device that does not create a blood-air interface and does not disturb the blood flow. The pump pressure signal is used by the microprocessor to determine TMP used to calculate the ultrafiltration rate. It is also used to detect abnormal conditions in the circuit such as occlusion or unacceptable clotting of the filter and disconnection of the blood line between the pump 204 and the filter 207.

On its way from the pump 204 to the filter 207, blood passes through the air detector 206. The air detector 206 is of ultrasonic type and can detect air in amounts exceeding approximately 50 microliters. The detector 206 uses technology based on the difference of the speed of sound in liquid and in gaseous media. If an air bubble is detected, the pump 204 is stopped almost instantaneously (within few milliseconds). The bubble detector output signal is hard wired into the motor control logic and the pump 204 is stopped independently of the microprocessor control if a bubble is detected.

Air can only enter the present invention circuit from the pre-pump (negative pressure) segment of the blood circuit 202. All the rest of the circuit downstream of the pump 204 is always pressurized. For this reason, the bubble detector is placed before the filter.

Blood pressure in the post pump, pre-filter segment of the circuit is determined by the patient's venous pressure, the resistance to flow generated by the return needle 210, resistance of hollow fibers in the filter assembly 207 and the resistance of interconnecting tubing 208. At blood flows of 40 to 60 mL/min the pump pressure is in the 300 to 500 mmHg range depending on the blood flow, condition of the filter, blood viscosity and the conditions in the patient's vein.

The filter 207 is a main component of the present invention. Inside the filter 207 the ultrafiltration occurs. Whole blood enters the bundle of hollow fibers from the connector on the top of the cap of the filter canister. There are approximately 700 hollow fibers in the bundle, and each fiber is a filter. Blood flows through a channel approximately 0.2 mm in diameter in each fiber. The walls of the channel are made of a porous material. The pores are permeable to water and small solutes but impermeable to red blood cells, proteins and other blood components that are larger than 50,000–60,000 Daltons. Blood flow in fibers is tangential to the surface of the filter membrane. The shear rate resulting from the blood velocity is high enough such that the pores in the membrane are protected from fouling by particles, allowing the filtrate to permeate the fiber wall. Filtrate (ultrafiltrate) leaves the fiber bundle and is collected in space between the inner wall of the canister and outer walls of the fibers.

The geometry of the present invention filter is optimized to prevent clotting and fouling of the membrane. The active area of the filter membrane is approximately 0.1 m². The permeability KUF of the membrane is 30 to 33 mL/hour/m²/mmHg. These parameters allow the desired ultrafiltration rate of approximately 500 mL/min at the TMP of 150 to 250 mmHg that is generated by the resistance to flow. The effective filter length is 22.5 cm and the diameter of the filter fiber bundle is 1.2 cm. This results in the shear rate of 1,200 to 1,800 $sec^{-1}$ at the blood flow rate of 40 to 60 mL/min.

The TMP in the present invention is defined predominantly by the resistance of the return needle 210 and the resistance of the filter bundle inside the filter 207. The properties of the filter 207 and the needle 210 are selected to assure the desired TMP of 150 to 250 mmHg at blood flow of 40–60 mL/min where blood has hematocrit of 35 to 50% at 37° C.

The quantitative clinical goal was formulated for the apparatus being developed in terms of fluid removal. Applicants' research established that for the fluid removal device to be clinically useful it should remove water at the rate of 100 to 500 mL/hour. Lower rates of fluid removal are only required in hemodynamically unstable patients that are treated in the ICU and are not the targeted patient population. Fluid removal rates higher than 500 mL/hour (theoretically as high as 1,000 mL/hour) may be practical in some patients but are expected to be too high risk in the majority. It is only advisable to remove water from blood at the rate at which fluid can be recruited from tissue. Higher rates may lead to hypotension.

Blood hematocrit (volume fraction of red blood cells) in CHF patients is expected to be in the range of 30 to 40% of the total blood volume. It is possible to condense the filtered blood to the hematocrit range of 50% to 60% and still be able to return blood through a standard needle. Therefore, extraction of approximately 20% to 30% of volume from blood as water is possible. Assuming this extraction rate, the amount of blood removed from a peripheral vein is less than 2% of the total cardiac output. In addition, at this extraction rate, the potential ultrafiltrate flow may be as much as 1 L/hour. Alternatively, a lower extraction rate, e.g., 0.1 liter/hour, may be selected. At the blood flow rate of 60 mL/min applicants successfully extracted up to 12 mL/min (or 720 mL/hour) of ultrafiltrate in the laboratory using the filter described here. Therefore, it is possible to consistently extract the required 500 mL/hour of water from the blood flow withdrawn and returned into a peripheral vein.

Applicants established that the much higher blood flows that are used in adults by all existing renal replacement therapy machines and particularly by machines for acute CVVH treatment of CHF patients are necessitated by the filter designed to remove solute and more specifically by the relatively high surface area of the filter. This large surface area is needed for solute removal. If the goal of treatment was to remove water only, high blood flow will still be needed to reduce the time of exposure of blood to the synthetic membrane and to prevent clotting.

Another important consideration that forces the designers of CVVH machines to use high blood flow and consequentially the central venous access is the need to maintain substantially high wall shear rate of blood flowing inside the filter capillaries (hollow fibers). Flow of blood inside a fiber is laminar. Shear rate at the wall can be calculated using the simple Equation 1:

$$y = 32 \times Q/(d^3 \times pi) \qquad \text{(Equation 1)}$$

Q is blood volumetric mass flow rate and "d" is the internal diameter of the capillary.

The ultrafiltration rate is influenced by membrane fouling which is an equilibrium of wall shear rate and ultrafiltration rate per unit surface area. With the increasing surface area the wall shear rate will decrease unless the blood flow is increased to compensate. It becomes apparent from literature that the wall shear rate should be 1,000 $sec^{-1}$ or higher to achieve sufficient filtrate flux at high hematocrit. It is also known from literature that the high shear rate in excess of 2,500 $sec^{-1}$ is undesirable since it can cause hemolyisis and damage to red blood cells. At the same time, it is apparent that the surface area and size of the filter should be minimized. Biocompatibility is inversely proportional to the surface area exposed to blood. The likelihood of clotting increases with residence time proportional to the filling volume. Also, cost of a smaller filter is lower.

To minimize the cost of the filter, the use of commercially-available fibers with optimized biocompatibility and consistent filtration properties is desired. Suitable filter fiber is available, for example, from Minntech Inc. in Minnesota. Each fiber has internal diameter of 0.2 mm. Pores in the fiber walls are optimized to retain solutes of greater than 50,000 Daltons. The permeability of this fiber is 33 mL/hour/$m^2$/mmHg. If a membrane with total surface area of only 0.1 $m^2$ is constructed from this fiber, the resulting theoretical ultrafiltration rate will be 330 mL/hour at TMP of 100 mmHg and 660 mL/hour at TMP of 200 mmHg. These numbers are consistent with the objective of the design.

To calculate the KUF of the filter, the permeability of fiber is multiplied by the surface area of the membrane. Therefore KUF filter=33×0.1=3.3 mL/hour/mmHg.

It is known from literature that the blood flow is not equal between the fibers in the filter bundle. Blood flow and consequentially the wall shear rate tends to be lower in the fibers closer to the periphery and higher in the central ones. Accordingly, blood residence time is longer in peripheral fibers. It is known from the practice of dialysis that the peripheral fibers tend to clot first.

To reduce the extracorporeal blood volume and the time that blood resides outside of the body it is desired to use blood lines that have internal diameter as small as practical without creating excessive resistance to flow. For our application, an internal diameter of around 3.0 mm is well suited. When blood exits the tubing and flows into the fiber bundle the diameter of the channel through which blood flows increases substantially. This creates turbulence and stagnant zones at the entrance into the bundle. These factors increase the probability of clotting.

It is therefore beneficial to design a filter that has a minimal but still practical diameter of the fiber bundle. This is achieved by reducing the number of fibers and increasing the length of the bundle. This approach is limited by two constraints. Resistance of the bundle to flow increases in proportion to the bundle length. Also, long filters substantially in access of 20–25 cm are difficult to manufacture and cumbersome to use.

Applicants chose to use a maximum length of the filter that is practical from the manufacturing standpoint. The resulting working length of the bundle is 22 cm (centimeters). To ensure the required surface area of the membrane, approximately 620 to 720 fibers of this length are need to be bundled in parallel. Assuming the fiber density of approximately 630 capillaries per $cm^2$ the diameter of the bundle is 1.2 cm. Such filter can be easily manufactured using existing methods and equipment. At the blood flow of 40 to 60 mL/min and blood hematocrit of approximately 40%, the resistance of this filter to blood flow is on the order of 100 to 200 mmHg. This pressure level is acceptable for the design of a circuit with a standard peristaltic pump and an 18 to 20 Gage (internal diameter of 0.8–1.0 mm) return needle.

Applicants overcame the perceived impossibility of clinical peripheral vein ultrafiltration that limited the use of mechanical fluid removal in CHF patients outside of the ICU environment. Applicants did this by drastically reducing the filter membrane surface area compared to common dialysis or CVVH filters to maintain high shear rate and low blood residence time. Specifically, a filter with the membrane surface of less than 0.2 $m^2$ and preferably 0.05 to 0.15 $m^2$ can remove the desired 100 to 700 mL/hour of water from the extracorporeal blood flow of less than 100 mL/min or more specifically of 40 to 60 mL/min with an average blood cell residence time outside the body of less than 2 minutes, and may be less than 1 minute. Although the filter is made of high permeability fiber due to the small surface area the KUF of the filter is less than 5 mL/hour/mmHg or preferably 2 to 4 mL/hour/mmHg. Typical filters used in adult patients have KUF of 30 to 50 mL/hour/mmHg. The much lower KUF gives the present invention device design an advantage of inherently safer operation. Food and Drug Administration (FDA) classifies all filters with KUF greater than 8 mL/hour/mmHg as "high permeability dialyzers". According to current FDA safety standards these devices have to be labeled for use only with ultrafiltration controllers that are independent of TMP based ultrafiltrate rate calculation. A small error of TMP measurement or a deviation of membrane permeability from the specification can result in substantial over or under filtration. The use of a low KUF filter enables, if desired, the present invention to avoid using a cumbersome and expensive ultrafiltration controller that typically involves a scale balance and an ultrafiltration pump.

A filter that is relatively long and narrow may optimize the blood flow inside the filter, maintain the desired wall shear rate and minimize membrane fouling and filter clotting. A filter with a fiber bundle that is approximately 20 cm long and 1.5 cm in diameter is particularly well suited for the application and is practical for manufacturing.

Filters for ultrafiltration of blood with small surface area of less than 0.2 $m^2$ are known. Example of such filter is Miniflow™ 10 from Hospal. Miniflow has surface area of 0.042 $m^2$ and KUF of 0.87 mL/hour/mmHg. All such filters without exception are used for hemofiltration therapy in neonatal patients and infants. The clinically used amount of blood flow through these filters is within the range that we targeted or 10 to 60 mL/min. Nevertheless, this amount of flow—if expressed as a fraction of the cardiac output for infants—is the same as the blood flow used in adult hemofiltration. Consequently, these infant filters are used with the central and not peripheral venous access.

To minimize clotting and fouling of the membrane it is desired to maintain substantially high blood flow through the filter even if the desired ultrafiltration rate is low. In traditional machines for renal replacement therapy it is typically achieved by reducing the TMP. Flow of ultrafiltrate is actively controlled by the roller pump in the ultrafiltrate removal line between the filter and the ultrafiltrate collection bag. When the pump is slowed down ultrafiltrate flow is retarded, pressure gradient across the membrane is reduced and ultrafiltration is slowed to the desired level. Alternatively, if the pump RPM is increased, the flow of ultrafiltrate is accelerated. Negative pressure can be developed by the pump to actively suck the ultrafiltrate across the membrane. For reasons of safety and simplicity, it was desired to have a machine that can reduce the ultrafiltration rate at the user command without an ultrafiltrate pump. For our preferred embodiment we used the duty cycle controlled ultrafiltration. A simple pinch valve is placed in the ultrafiltrate line. When the valve is closed, pressure across the membrane quickly equilibrates, and no ultrafiltration occurs. When the valve is opened, ultrafiltration occurs at the rate determined by the TMP and the KUF of the membrane. This rate can be calculated by the controller. Valve is cycled approximately every minute. The fraction of the cycle during which the valve remains opened determines the average rate at which fluid is removed.

Since the system embodying the present invention does not employ an ultrafiltrate pump that can create sub-atmospheric pressure on the ultrafiltrate side of the membrane, a simple and reliable method of controlling the total amount of fluid removed in one treatment iteration is possible. The ultrafiltrate is collected into a sealed bag that is connected by a tube to the ultrafiltrate collection chamber of the filter casing. During the treatment the bag is gradually filled up with fluid. It is desired to have a bag that has a relatively small volume and specifically volume of 0.5 to 1.5 liters. When the bag is full and its walls are fully distended, the pressure in the bag will start to rise until it is equal to the average pressure of blood inside the filter capillaries. Although some circulation of fluid is still possible in and out of fibers the net loss of fluid is zero. Until a nurse empties the bag, no removal of fluid is possible.

Pressure sensors are used in the blood circuit to alarm the disconnection and occlusion of blood lines. The pre- and post-filter pressure signals are also used to calculate TMP and ultrafiltration rate. Two types of pressure measurement devices are typically used in machines for renal replacement therapy.

Machines such as BP11 from Baxter use disposable air filled separation or drip chambers that are connected to permanently installed pressure sensors that are the part of the machine. This design introduces potentially hazardous air into the circuit. Air can cause embolism and accelerated clotting. Also, this type of measurement is affected by gravity.

Machines such as Prisma from Gambro use flexible silicone diaphragms to transmit blood pressure to sensors once again mounted on the apparatus itself. This method overcomes the deficiencies of drip chambers. Separation diaphragms are subject to error when the travel of a diaphragm is restricted. This necessitated a complicated diaphragm positioning system if the system is used for a substantial duration of time. Also, a substantial area of a diaphragm (typically 2–3 cm in diameter) is required to ensure reliable transmission of pressure. At a low blood flow it is likely that a stagnant zone will form inside the diaphragm chamber that will eventually lead to clotting.

The present invention utilizes flow through disposable pressure sensors. This sensors are a part of the disposable blood circuit. They do not disturb the laminar blood flow inside the blood line since the internal diameter of the sensor element is the same as of the blood tubing (3 mm). The sensing element is less than 2 mm in diameter and is embedded flush in the wall of the sensor housing. The housing is bonded flush with the internal wall of the blood line tube to form a continuous channel. Although similar disposable blood pressure sensors (such as ones made by Merit Medical of Utah) are used widely for invasive blood pressure measurement this design has never been previously used in an apparatus for fluid removal.

The present invention is intended to provide safe, controlled fluid removal in patients with fluid overload for up to 8 to 24 hours. These patients all suffer from decompensated chronic CHF and are admitted or on the verge of admission to a hospital. Regardless of the exact nature of their disease theses patients present at the hospital with a number of symptoms that manifest fluid overload and result in difficulty of breathing and pulmonary edema require immediate treatment. These patients are typically 5 to 20 kg over their dry weight and, if treated with diuretics, can tolerate fluid removal rates of up to 0.5 L/hour for until symptoms are relieved.

The intended use of the present invention is to assist in the initial removal of 2 to 4 liters of fluid that should result in the relief of symptoms and much improved responsiveness to medication. The present invention can be performed by a physician or nurse trained in the use of the device. Treatment can be performed in the setting of a monitored hospital floor, outpatient clinic or Emergency Room. The present invention is prescribed by a cardiologist. The main idea behind the present invention is to remove excess water from the patient's blood using a well-accepted ultrafiltration technique at the same rate at which the surplus fluid can be recruited from the tissue.

The intended use of the present invention is slow continuous removal of fluid by ultrafiltration of blood. Excessive removal of fluid can lead to hypotension and serious risks to health. If the fluid is removed from vascular space too fast, it is equally dangerous and can lead to hypotension. The principle method of treatment with the present invention is to remove fluid at a rate that allows vascular blood volume to be replenished with water that has accumulated in the interstitial space as a result of the patient's condition. Patients that should be treated by the present invention are typically 10 to 20 kg over their dry weight due to this excess water.

Potential excessive water loss or gain is a recognized hazard associated with RRT. Modern CRRT machines used in SCUF or CVVH mode can potentially remove and replace tens of liters of fluid from patient in a space of several hours. As a result, even a small error in fluid balance can result in severe risks to a patient. To prevent this from happening accurate ultrafiltration controllers are used that are based on continuous measurement of the weight of extracted and infused fluids. Ultrafiltration rate is adjusted accordingly by controlling the speed of an ultrafiltration pump that can apply negative or positive pressure to the ultrafiltrate side of the filter membrane.

In the case of the present invention, fluid gain is not a risk. The present invention is designed for fluid removal only. To prevent excessive removal of fluid from the patient, the present invention relies on a number of inherently safe features and materials properties rather than the ultrafiltrate pump controller.

Ultrafiltrate rate (UF) is a function of TMP, Permeability of the membrane and the membrane surface. Membrane surface is a constant and in the case of the present invention is 0.1 m$^2$. Permeability of a filter membrane is expressed as ml of ultrafiltrate per hour per unit of the membrane surface area, and may be 30 to 33 mL/hour/m$^2$/mmHg. The resulting KUF of the filter may be 3 mL/hr/mmHg. KUF of a filter can decrease during the operation owing to the fouling of the membrane but can not increase unless the membrane is broken. Equation 2 takes into account the affects of oncotic pressure on the ultrafiltration rate. The KUF of the membrane is determined using animal blood at standard conditions such as hematocrit of 27%, temperature of 37° C. and appropriate concentration of protein and electrolytes. Although these conditions do not perfectly reflect clinical conditions in all patients it is a useful engineering approximation.

$$UF = TMP \times (KUF \times \text{Area}) \qquad \text{(Equation 2)}$$

In the present invention, TMP is a function of blood flow and the resistance of circuit elements downstream, including the filter. TPM can be calculated in real time by the microprocessor using equation 3 from the readings of pressure transducers.

$$TMP = (Pp - Pr)/2 + Pr - Pg \qquad \text{(Equation 3)}$$

Where Pp is the pump (pre filter) pressure, Pr is the return (post filter) pressure and Pg is a pressure generated by the weight of the column of ultrafiltrate. Given the unadjustable design of the ultrafiltrate circuit, Pg is a constant. For the 20 cm level difference between the filter and the level of fluid in the bag Pg is 17 mmHg.

Substitution of the calculated TMP into Equation 2 gives a reasonable estimate of the ultrafiltration rate.

During the use of the present invention the operator sets the maximum allowed rate of ultrafiltration in mL/hour. Values between 100 and 500 mL/hour are allowed. The present invention microprocessor establishes the rate of withdrawal of blood in the range of 40 to 60 mL/min. This flow rate is determined by the quality of access. It is advantageous to establish and maintain blood flow constant.

Based on the pressure sensor readings the TMP is calculated. This allows the calculation of ultrafiltrate rate for known KUF of the filter.

If the ultrafiltration rate is higher than desired it is reduced using the solenoid ultrafiltrate pinch valve 213 in FIG. 2. When the valve 213 is closed the pressure inside the ultrafiltrate compartment of the filter 6 rises rapidly until it is equal to the pressure in the blood compartment (fibers). When the system is in equilibrium, no ultrafiltration occurs. The pinch valve 213 is cycled approximately once per minute. The duty cycle (ratio of open to closed state) is calculated ratiometrically from the actual and desired ultrafiltration rate.

Figure 3:
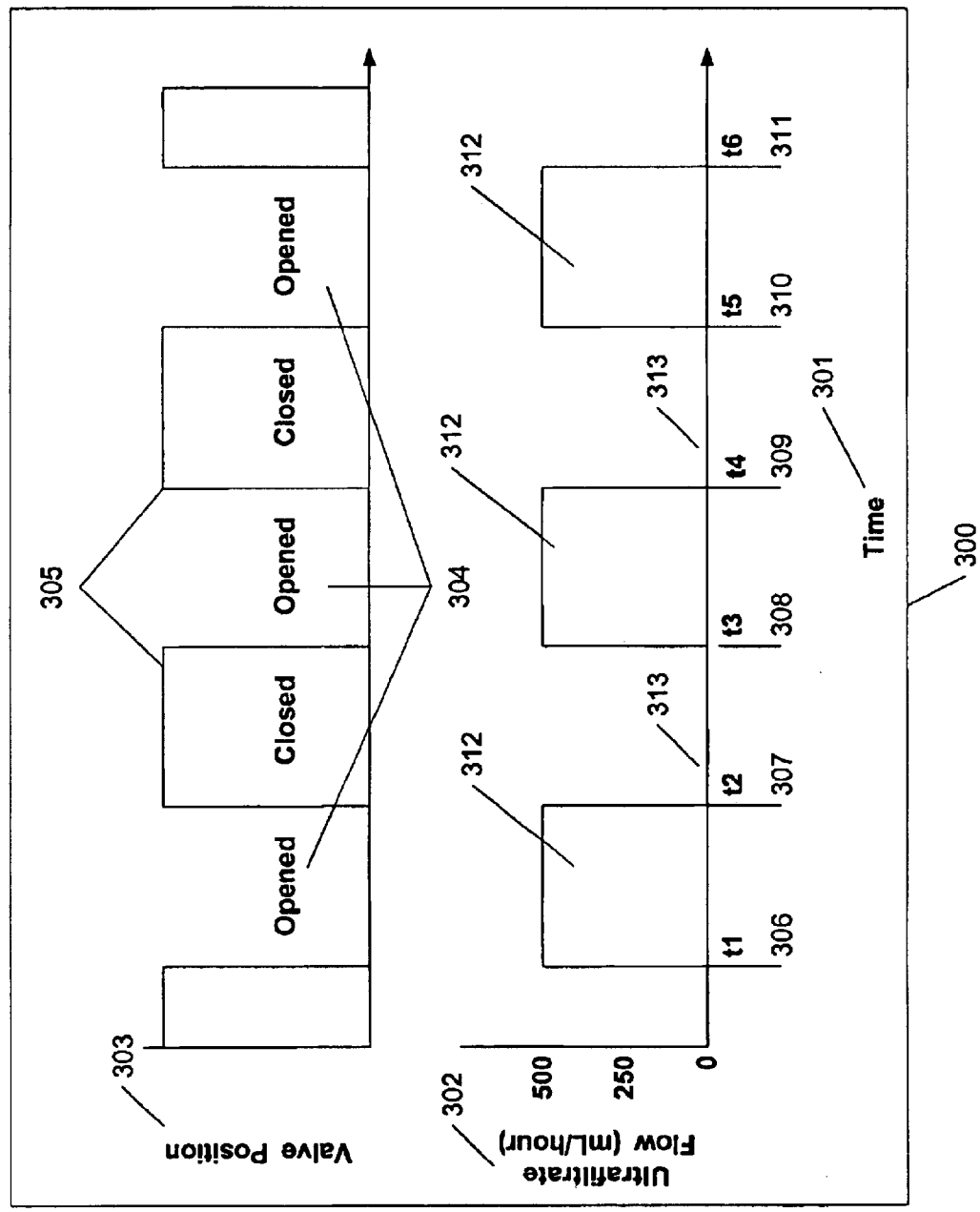
FIG. 3 is a graphical illustration tracing how the desired average ultrafiltration rate of 250 mL/hour is achieved with a 50% duty cycle control.

Traces on FIG. 3 illustrate how the desired average ultrafiltration rate of 250 mL/hour is achieved with a 50% duty cycle control. In FIG. 3, graph 300 shows time 301 versus ultrafiltrate flow rate 302. Times $t_1$ 306, $t_2$ 307, $t_3$ 308, $t_4$ 309, $t_5$ 310 and $t_6$ 311 are evenly spaced with equal periods between them. The valve position 303 shows during which periods the valve 213 is open 304 and closed 305. For example, between time $t_1$ 306 and time $t_2$ 307, valve 213 is open, but between time $t_2$ 307 and time $t_3$ 308, valve 213 is closed. For example, when the valve is opened ultrafiltrate flow is 500 mL/min, shown by lines 312. When the valve is closed it is zero, shown by lines 313. Thus, using equal periods of opened valve 213 and closed valve 213 will effectively achieve an average flow rate equal to half of the open valve flow rate.

Other factors limiting the ultrafiltration rate are the amount of blood available for filtration and the hematocrit of the blood entering the filter. Equation 4 can be used to calculate the return blood hematocrit HR from the blood flow BF, ultrafiltrate flow UF and withdrawal blood hemotocrit HW.

$$UF=BF\times(HR-HW)/HW \qquad \text{(Equation 4)}$$

The safe pump 204 can deliver up to 60 mL/min of blood. The maximum amount of water that can be extracted from the blood is determined by the hematocrit of the return blood. As the water is extracted, hematocrit increases. This in turn increases the viscosity of blood. Blood entering the filter typically has hemotocrit of 35 to 45%. The corresponding viscosity is approximately 3 to 4 mPa-s. Viscosity of blood with the hematocrit of 60% is 6 mPa-s. At 70% hematocrit blood becomes too viscous to pass through the filter or the return needle.

The volume of the ultrafiltrate collection bag 215 determines total amount of fluid removed from the patient. The bag 215 is connected to the fluid removal port 211 of the filter 207 by the bonded PVC tube 212. The ultrafiltrate collection system is sealed. When the bag is full, the pressure in the bag 215 rises until it is equal to the average pressure of blood in the filter fibers. Ultrafiltration is stopped until the bag is emptied by the operator by opening the ultrafiltrate valve 216. The volume of the ultrafiltrate bag 215 is one liter. This automatically limits the maximum amount of water that can be removed from the patient without an operator's interaction. Bag 215 is transparent and has volume marks that allow user to read the actual amount of fluid removed in preferably 100 mL increments.

Blood exiting the filter 207 through the connector on the bottom of the filter casing is continuously returned to the patient through the return needle 210. Blood flow leaving the filter is the same as the blood flow entering the filter if the ultrafiltrate clamp 213 is closed. If the clamp 213 is open ultrafiltration occurs and the blood is continuously fractured into the ultrafiltrate and more concentrated blood. The hematocrit and the volume of returned blood are determined by the ultrafiltration fraction, which is the volumetric fraction of the ultrafiltrate relative to the volume of whole blood entering the filter.

Blood return circuit pressure sensor 209 serves several functions. The return pressure is used in the TMP calculation that is in turn used to calculate input data for the control of the ultrafiltration rate. It is also used to detect a disconnected or occluded circuit. Excessive pressure signals the occlusion that can be caused by a kinked tube or a clotted needle. Since the resistance of the needle 210 is much higher than the resistance of the blood line 208, disconnection of the needle from the tubing is easy to detect from an abrupt drop of the return pressure.

Figure 4:
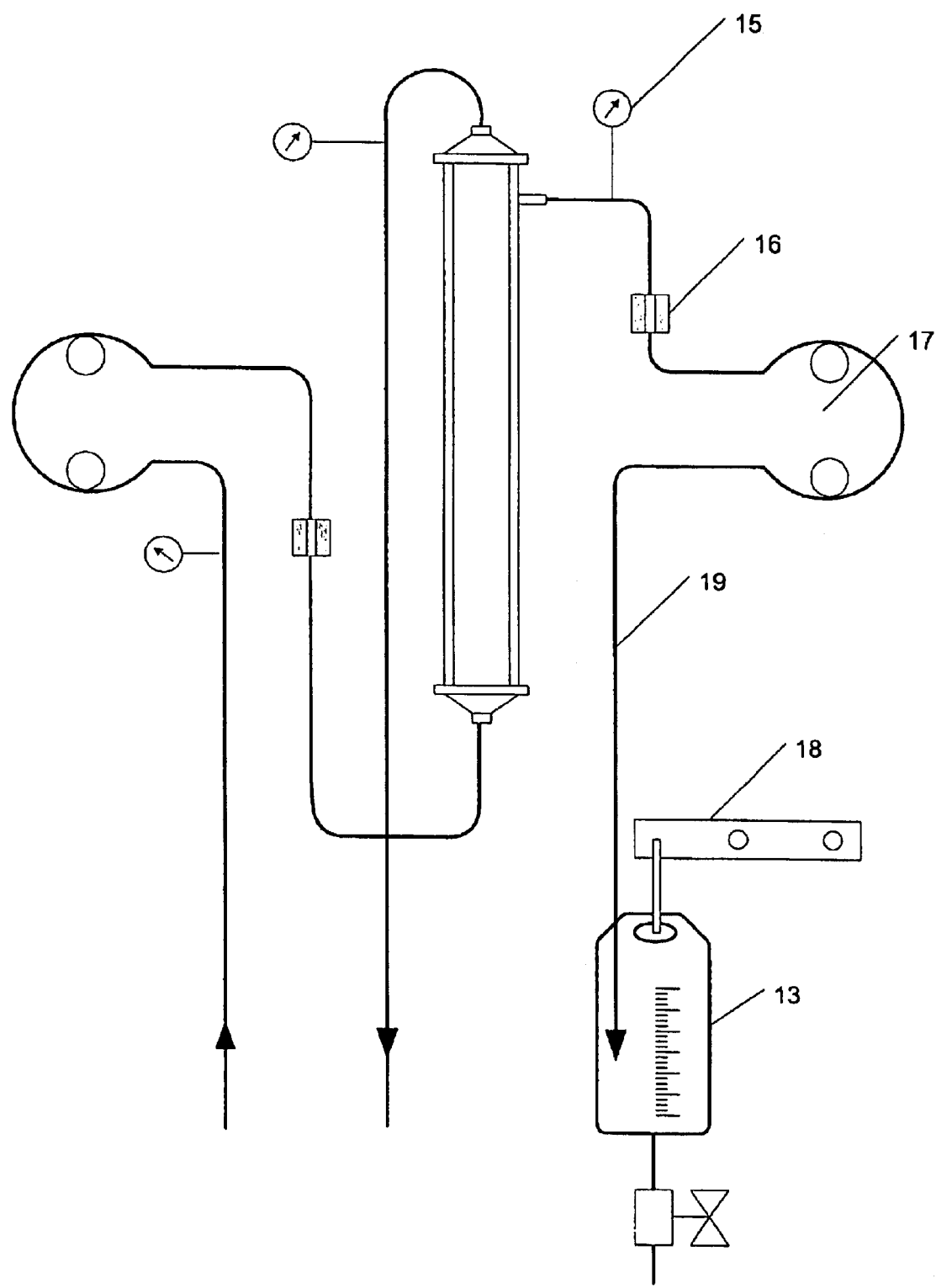
FIG. 4 illustrates another embodiment of the invention when more precise removal of fluid is desired.

FIG. 4 shows another embodiment of the invention. This embodiment is preferred when more precise removal of fluid is desired. An ultrafiltrate pump 17 is used to pump and meter ultrafiltrate into the collection bag 13. Weight scale 18 allows additional control and monitoring of the amount of the removed fluid. Ultrafiltrate pressure sensor 15 is used to monitor the TMP and to detect clotting or fouling of the filter. Blood leak sensor 16 is used to detect the leakage of red blood cells across the filter membrane if the membrane is damaged. The blood sensor is of photometric type and responded to the change of color of the ultrafiltrate.

Figure 5:
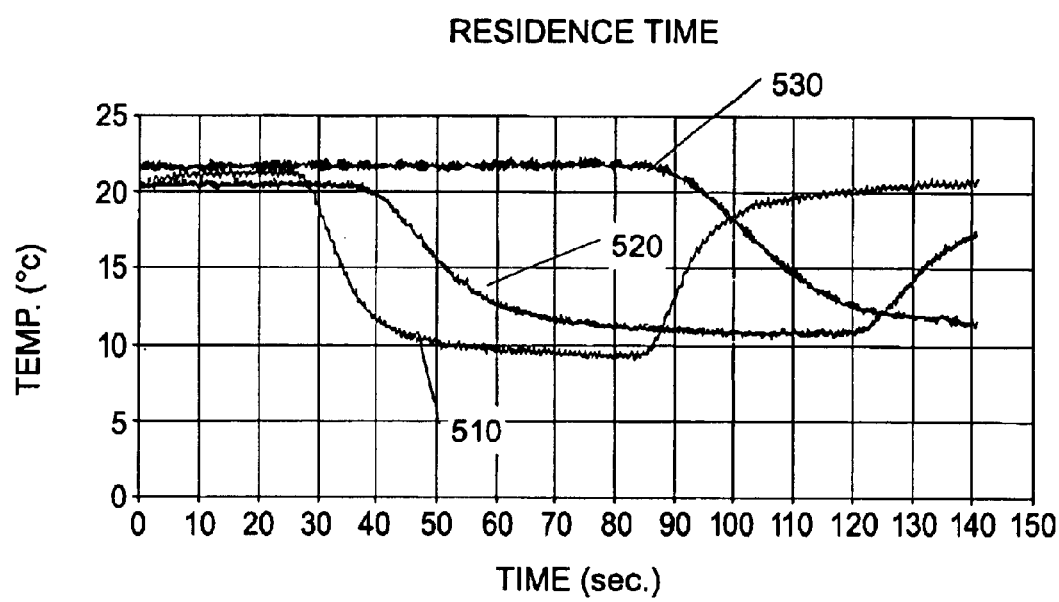
FIG. 5 is a graph comparing the effect of the reduction of the filter membrane area on the residence time of blood by comparing transit time of blood in contact with plastic tubing, a standard F40 filter, and the filter described in this invention.

FIG. 5 illustrates the effect of the reduction of the filter membrane area on the transient time of blood in contact with plastic. Experiments were performed using the thermodilution method. At the time mark 0 iced water flowing through the system at 60 mL/min replaced the room temperature water. Three curves show the time delay before the cold water reached the exit of the circuit (simulated return of blood to the patient). Curve 510 corresponds to a continuous 2 meter long tube with internal diameter of 3 mm with no filter at all. Curve 520 is the filter described in this invention. Curve 530 is the standard F40 filter by Frescenious. Traces show that the time of contact of blood with plastic during the treatment with proposed invention will be significantly shorter than that with a conventional dialysis machine.

Figure 6:
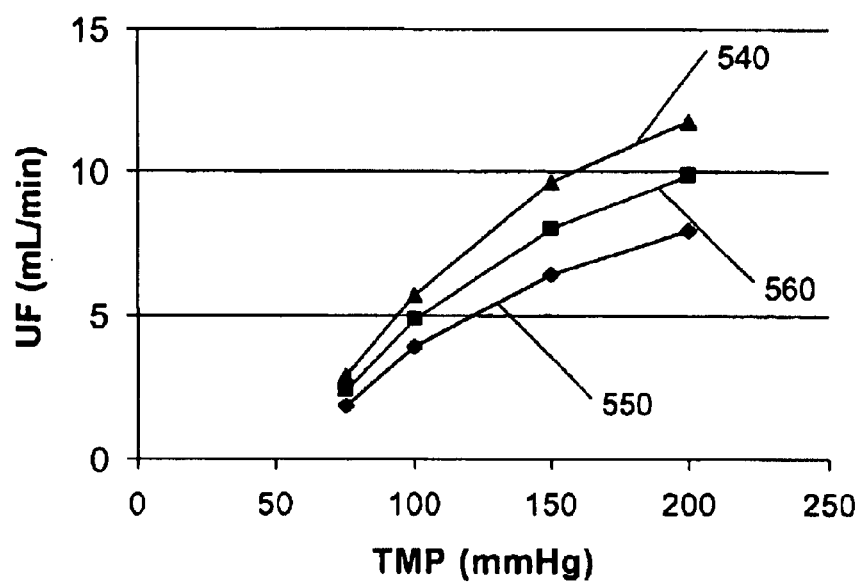
FIG. 6 is a graphical representation illustrating that the desired amount of ultrafiltrate can be removed with the filter described in the preferred embodiment.

FIG. 6 proves that the desired amount of ultrafiltrate can be removed with the filter described in the preferred embodiment. Curves 560, 550 and 540 correspond to blood flows of 40, 50 and 60 mL/min accordingly. Animal blood with hematocrit of 27% at the temperature of 37° C. was used in the experiment. TMP was between 100 and 250 mm Hg and shear rate of blood inside the filter was maintained in the 1000 to 2000 $sec^{-1}$ range. The desired amount of 5–10 mL/min of ultrafiltrate was filtered out of blood before it was returned into a vessel using a 18 Gage needle. Filter had surface are of 0.1 $m^2$ with membrane permeability of 33 mL/hr/$m^2$/mmHg supplied by Minntech. Filter bundle was made out of 700 fibers 22 cm long as described previously in this invention.

Figure 7:
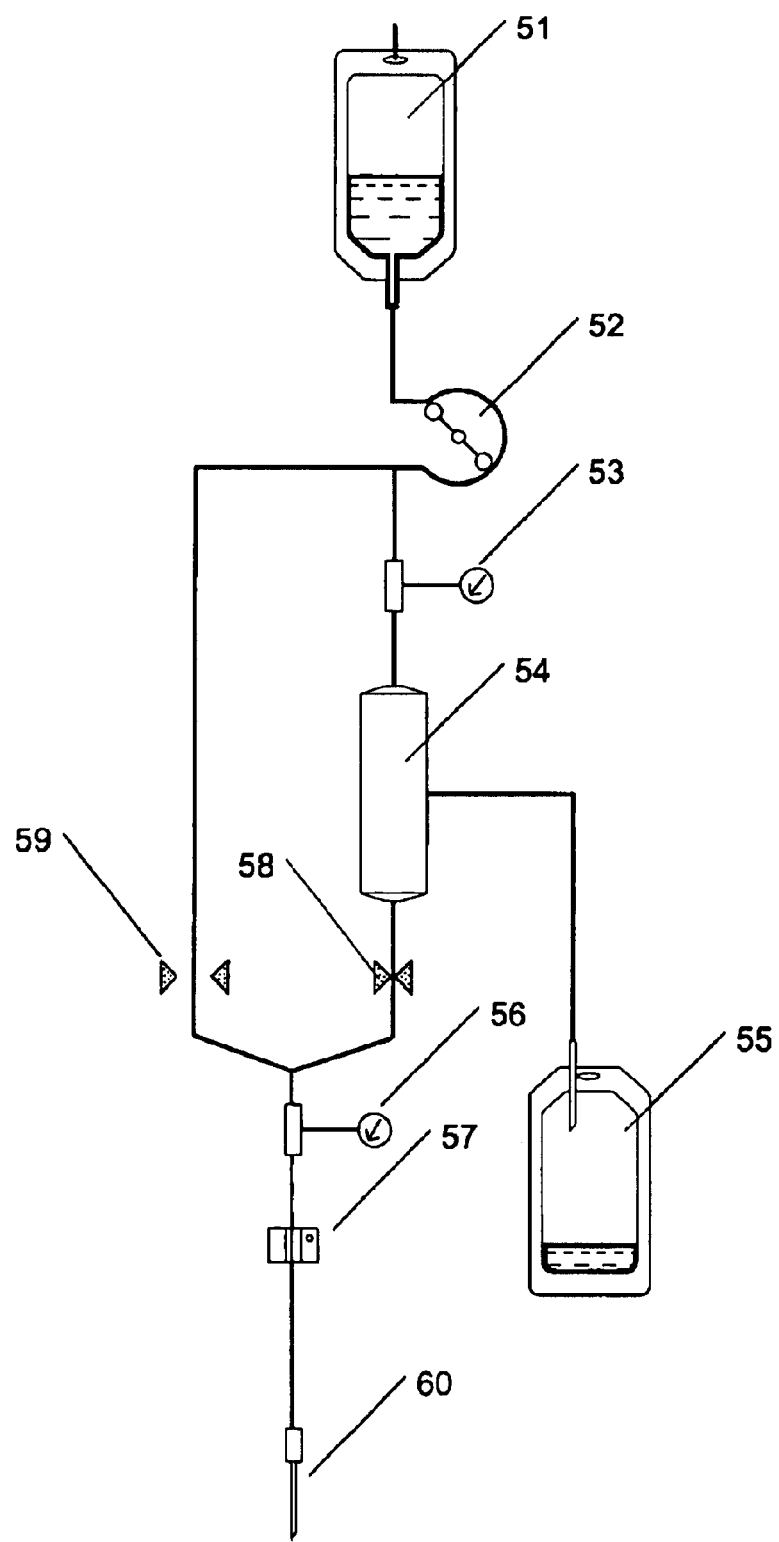
FIG. 7 is an illustration of another embodiment of the invention with an apparatus designed for removing blood in a batch type process using a single needle and blood storage bag.

FIG. 7 shows yet another potential embodiment of the invention. This apparatus is of a batch type and uses one needle 60. Blood is withdrawn from the vein and stored in the bag 51. During the withdrawal phase roller pump 52 rotates counter clockwise. Approximately 50 mL of blood can be stored in the bag 51. Valve 59 is open and valve 58 is closed so that the filter 54 is bypassed. Blood is then ejected from the bag 51 through the filter 54 back into the patient's vein through the needle 60. Valve 58 is opened and valve 59 is closed and the pump 52 rotates clock wise. During this phase filtration occurs and the ultrafiltrate is collected in the bag 55. Pressure sensors 53 and 56 are used to control the process so that vein does not collapse or overextend and TMP is not too high. Air detector 57 is used to protect the patient from embolism. An anti-coagulant may be needed in view of the temporary storage of blood in the bag 51.

The invention has been described in connection with the best mode now known to the applicant inventors. The invention is not to be limited to the disclosed embodiment. Rather, the invention covers all of various modifications and equivalent arrangements included within the spirit and scope of the appended claims.

What is claimed is:

1. A method for removing excess fluid from a patient comprising:
    a. inserting a withdrawal catheter into a first peripheral blood vessel in the patient;
    b. withdrawing blood through the catheter in the first peripheral blood vessel in the patient;
    c. sensing a withdrawal pressure of the blood;
    d. adjusting a withdrawal blood flow rate based on the sensed withdrawal pressure;
    e. filtering the withdrawn blood through a filter to separate the excess fluid from the blood, wherein the filter has a filter membrane surface area of no greater than 0.2 m$^2$;
    f. infusing the filtered blood into a second peripheral blood vessel in the patient;
    g. wherein a blood flow through the filter is less than two percent of a total cardiac output of the patient, and a flow of the excess fluid removed from the blood is no greater than 1.0 liters per hour.

2. A method as in claim 1 wherein the excess fluid removed from the blood is no greater than 30 percent of a volume of the removed blood.

3. A method as in claim 1 wherein the step of filtering is performed by sieving the blood through a filter to remove excess fluid.

4. A method as in claim 1 further comprising the step of pumping the withdrawn blood with a blood pump at a rate of less than 100 milliliters (ml) per minute.

5. A method as in claim 1 wherein a rate of blood withdrawal is in a range of 40 to 60 milliliters per minute, and a rate of removal of the excess fluid is no greater than 16 milliliters per minute.

6. A method as in claim 4 wherein the blood pump stops upon detection of a blockage of blood flow in the blood being withdrawn.

7. A method as in claim 1 wherein the blood pump stops upon detection of a air bubble in the withdrawn or filtered blood.

8. A method as in claim 1 wherein the first peripheral blood vessel is a vein.

9. A method as in claim 1 wherein the second peripheral blood vessel is a vein.

10. A method as in claim 1 wherein the first and second peripheral blood vessel are the same vein.

11. A method as in claim 1 wherein the filter includes capillary, hollow fibers.

12. A method as in claim 11 wherein the hollow fibers have filtering pores which retain in the blood solutes greater than 50,000 Daltons.

13. A method as in claim 11 wherein the hollow fibers have blood passages of approximately 0.2 mm or less in diameter.

14. A method as in claim 1 wherein the blood flow through the filter causes a wall shear rate of the blood between 1,000 sec$^{-1}$ per seconds and 2,500 per seconds.

15. A method as in claim 1 wherein the filtration is ultrafiltration.

16. A method as in claim 1 further comprising minimizing extraction of solutes during filtration.

17. A method as in claim 1 further comprising extracting primarily water as the fluid removed from the blood during filtration.

18. A method as in claim 1 wherein blood flows continuously through the filter during periods in which a blood pump is pumping the removed blood.

19. A method as in claim 1 wherein excess fluid removed from blood flows intermittently from the filter.

20. A method as in claim 19 wherein a valve in a flow path from the filter for removal of excess fluid cyclically stops and starts the flow of excess fluid from the filter.

21. A method as in claim 1 wherein a total amount of extracorporeal blood is not greater than 100 milliliters.

22. A method as in claim 1 wherein said fiber includes less than 1000 filtering fibers.

23. A method as in claim 1 wherein the withdrawn blood is returned to the patient within two minutes.

24. A method for removing excess fluid from a patient comprising:
    a. withdrawing blood from a catheter inserted into a first blood vessel of the patient;
    b. monitoring a pressure of the blood being withdrawn and controlling a blood withdrawal rate based on the monitored pressure;
    c. condensing the withdrawn blood through a filter to separate the excess water from the blood, wherein the filter has filter membrane surface area of no greater than 0.2 m$^2$;
    d. returning the condensed blood into a second blood vessel in the patient;
    e. wherein a blood flow through the filter is less than two percent of a total cardiac output of the patient, and a flow of the excess fluid removed from the blood is no greater than 1.0 liters per hour.

25. A method as in claim 24 wherein the excess fluid removed from the blood is no greater than 30 percent of a volume of the removed blood.

26. A method as in claim 24 wherein the step of filtering is performed by sieving the blood through a filter to remove excess water.

27. A method as in claim 24 further comprising the step of pumping the removed blood with a blood pump at a rate of less than 100 milliliters (ml) per minute.

28. A method as in claim 24 wherein a rate of the removal of blood is no greater than 60 milliliters per minute, and a rate of removal of the excess water is no greater than 16 milliliters per minute.

29. A method as in claim 24 wherein a rate of the removal of blood is in a range of 40 to 60 milliliters per minute, and a rate of removal of the excess water is no greater than 16 milliliters per minute.

30. A method as in claim 27 wherein the blood pump stops upon detection of a blockage of blood flow in the blood being removed in step (b).

31. A method as in claim 27 wherein the blood pump stops upon detection of a air bubble in the blood during any of steps (b), (c) and (d).

32. A method as in claim 24 wherein the first blood vessel is a vein.

33. A method as in claim 24 wherein the second blood vessel is a vein.

34. A method as in claim 24 wherein the first and second blood vessels are the same vein.

35. A method as in claim 24 wherein the filter includes capillary, hollow fibers.

36. A method as in claim 35 wherein the hollow fibers have filtering pores which retain in the blood solutes greater than 50,000 Daltons.

37. A method as in claim 35 wherein the hollow fibers have blood passages of approximately 0.2 mm or less in diameter.

38. A method as in claim 34 wherein the filter has a trans-membrane pressure (TMP) no greater than 250 millimeters (mm) of mercury (Hg).

39. A method as in claim 24 wherein the blood flow through the filter causes a shear rate of the blood between 1,000 $\sec^{-1}$ per seconds and 2,500 per seconds.

40. A method as in claim 24 wherein the filtration is ultrafiltration.

41. A method as in claim 24 further comprising minimizing extraction of solutes during filtration.

42. A method as in claim 24 wherein blood flows continuously through the filter during periods in which a blood pump is pumping the removed blood.

43. A method as in claim 24 wherein excess water removed from the blood flows intermittently from the filter.

44. A method as in claim 43 wherein a valve in a flow path from the filter for removal of excess water cyclically stops and starts the flow of excess water from the filter.

* * * * *